United States Patent [19]

Brodie et al.

[11] Patent Number: 5,264,427
[45] Date of Patent: Nov. 23, 1993

[54] 20-SUBSTITUTED PREGNENE DERIVATIVES AND THEIR USE AS ANDROGEN SYNTHESIS INHIBITORS

[75] Inventors: Angela Brodie, Fulton; Jisong Li, Baltimore, both of Md.

[73] Assignee: Research Corporation Technologies, Inc., Tuscon, Ariz.

[21] Appl. No.: 827,040

[22] Filed: Jan. 29, 1992

[51] Int. Cl.$^5$ ............................................. A61K 31/56
[52] U.S. Cl. .................................. 514/177; 552/601; 552/602
[58] Field of Search ................ 514/177, 172; 552/601, 552/602

[56] References Cited

PUBLICATIONS

Krause, et al. *Steroids*, 31(6) pp. 823-839 (1978).
Li et al., *J. Steroid Biochem. Molec. Biol.*, 42: 313-320 (1992).

*Primary Examiner*—Marianne M. Cintins
*Assistant Examiner*—Kimberly J. Kestler
*Attorney, Agent, or Firm*—Dickstein, Shapiro & Morin

[57] ABSTRACT

Novel 20-substituted-pregnene derivatives, compositions containing such derivatives and methods for their use and manufacture are disclosed. The 20-substituted-pregnene derivatives inhibit the androgen biosynthesis enzymes 17(alpha)-hydroxylase/$C_{17,20}$-lyase and 5(alpha)-reducatase and are therefore useful for reducing or inhibiting production of androgens where they have an adverse role in a disease or physiological condition in vertebrate species.

5 Claims, 4 Drawing Sheets

20-SUBSTITUTED PREGNENE DERIVATIVES AND THEIR USE AS ANDROGEN SYNTHESIS INHIBITORS

This invention was made with government support under Contract No. CA-27740 awarded by the National Institute of Health. The government has certain rights in the invention.

FIELD OF THE INVENTION

This invention relates generally to androgen biosynthesis inhibitor compounds, compositions containing the inhibitor compounds, methods of manufacture, and methods of use; and specifically to 20-substituted-pregnene derivatives that have such inhibition activity.

REFERENCES

Several publications are referenced herein by Arabic numerals within brackets. All citations for these references may be found in the specification immediately proceeding the claims. The disclosures of these publications are hereby incorporated herein by reference in their entirety, unless otherwise noted.

BACKGROUND OF THE INVENTION

Androgen biosynthesis is mainly regulated by the steroid 17(alpha)-hydroxylase/$C_{17,20}$-lyase, which catalyzes the conversion of $C_{21}$ steroids precursors (pregnenolone and progesterone) to the related $C_{19}$ steroids (androgens) in the testis and adrenal gland. The principal androgen is testosterone. Effective inhibitors of this enzyme would be useful in investigating the physiological role of this enzyme complex and could be useful as a treatment for reducing production of androgens where they have an adverse role in diseases or conditions in vertebrates.

An important utility for such inhibitors may be the treatment of androgen-sensitive prostatic cancer in men. Patients with this disease respond to hormone ablative orchiectomy, but they eventually relapse. However, they may respond to subsequent and different types of hormonal therapy. While orchidectomy eliminates testicular androgens, adrenal androgens may continue to stimulate tumor growth. It is presently unclear whether total ablation of all androgens will be more successful than sequential treatment with different agents. In either case, new types of agents could be of benefit in treating this disease.

Several approaches are presently being used for the treatment of prostatic cancer. These include estrogens, antiandrogens, gonadotropin (LHRH) agonists and enzyme inhibitors.

A number of compounds that inhibit 17(alpha)-hydroxylase/$C_{17,20}$-lyase have been described [1-7], but most of these inhibitors are nonspecific and have low potency. Ketoconazole, an active imidazole fungicide, is currently being studied as a testosterone biosynthesis inhibitor [8,9], and it is used in the treatment of patients with advanced prostatic cancer [10,11]. However, this agent is not highly effective or specific. Also, it reduces cortisol production and has a number of side-effects.

In order to develop new inhibitors of 17(alpha)-hydroxylase/$C_{17,20}$-lyase, especially the $C_{17,20}$-lyase, we synthesized and tested a number of 20-substituted pregnene derivatives, based on the rationale that the modification of substrates at or close to positions which interact with the enzyme active site (i.e., the 20-position for the 17,20-lyase) may result in selective and potent inhibitors for this enzyme.

The 5(alpha)-reduction is a particularly important reaction occurring in the prostate. The enzyme 5(alpha)-reductase regulates the conversion of testosterone to dihydrotestosterone (DHT), which is responsible for the growth of the prostate. Since progesterone is an alternative substrate for the 5(alpha)-reductase, we also evaluated the use of the pregnene derivatives as inhibitors of this enzyme. Inhibition of 5(alpha)-reductase as well as 17(alpha)-hydroxylase/$C_{17,20}$-lyase would block all androgen synthesis, i.e., androstenedione, testosterone and dihydrotestosterone. Such inhibition could be an effective means of treatment for prostatic cancer patients.

Another utilization of these inhibitors might be the treatment of benign prostatic hyperlasia (BPH). Compounds that moderately reduce androgens and estrogens but are potent inhibitors or 5(alpha)-reductase may be effective in BPH, particularly in light of the fact that, in the prostate, DHT is the most active androgen. The known 5(alpha)-reductase inhibitors significantly increase plasma testosterone concentrations above the normal level. Some 20-substituted pregnenes which moderately inhibit the hydroxylase/lyase may serve to maintain normal levels of testosterone while reducing DHT levels.

There is a need to reduce the plasma levels of androgens to effectively treat excess androgens in females and androgen-sensitive cancers in males. In the female, this need can be met by providing compounds that inhibit the hydroxylase/lyase in adrenals and ovaries. In the male, this need can be met by providing compounds that inhibit both enzyme systems, i.e., hydroxylase/lyase in the adrenals and testes, thereby reducing plasma testosterone and androstenedione levels, and 5(alpha)-reductase in the prostate, thereby reducing production of prostatic DHT.

The present invention provides 20-substituted-pregnene derivatives that effectively inhibit both the 17(alpha)-hydroxylase/$C_{17,20}$-lyase and 5(alpha)-reductase enzymes and are therefore useful in reducing the production of androgens where they have an adverse role in a disease or physiological condition in vertebrate species.

SUMMARY OF THE INVENTION

It is an object of the invention to provide new androgen biosynthesis inhibitor compounds.

It is a further object of the invention to provide a composition for reducing or inhibiting the production of androgens in vertebrates.

Another object of the invention is to provide methods for synthesizing the new androgen biosynthesis inhibitor compounds.

A still further object of the invention is to provide compositions and methods useful as treatments for reducing or inhibiting the production of androgens or for treating androgen-sensitive cancers in vertebrates.

Additional objects and advantages of the invention will be set forth in part in the description that follows, and in part will be obvious on the description, or may be learned by the practice of the invention. The objects and advantages in the invention will be attained by means of the instrumentalities and combinations particularly pointed out in the appended claims.

To achieve the objects and in accordance with the purpose of the invention, as embodied and broadly described herein, the present invention provides for novel 20-substituted-pregnene derivatives of the following formula:

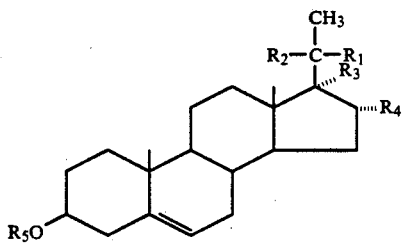

wherein $R_1$ and $R_2$ are a (20R)-20,21-epoxy, a (20S)-20,21epoxy, or $=N-N(CH_3)_2$, wherein $R_3$ and $R_4$ are both H or forming a 16,17-double bond, and wherein $R_5$ is H, a ($C_1$–$C_{10}$) carbonyl or a ($C_1$–$C_{10}$) alkyl.

The present invention also provides for novel 20-substituted-pregnene derivatives of the following formula:

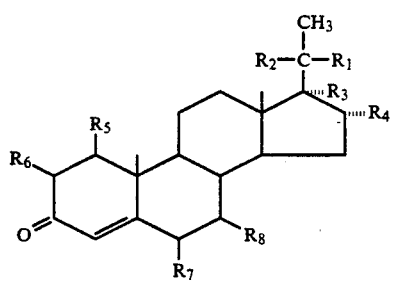

wherein $R_1$ is H, or $R_1$ and $R_3$ form a 17,20-double bond, $R_2$ is $-CH=N-N(CH_3)_2$, $20-C\equiv N$ $20$-$CH=NOY$, wherein Y is H or a $C_1$–$C_5$ alkyl, $R_4$ is H if there is a 17,20-double bond; alternatively $R_3$ and $R_4$ can form a 16,17-double bond; $R_5$, $R_6$ are both H or they form a 1,2-double bond, and $R_7$, $R_8$ are both H or they form a 6,7-double bond.

The present invention also provides for compositions for inhibiting androgen synthesis in vertebrates comprising compounds represented by the following formula:

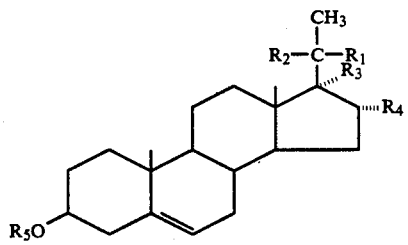

in which $R_1$ and $R_2$ are a (20R)-20,21-epoxy, a (20S)-20,21-epoxy, or $=NOY$, wherein Y is H or a $C_1$–$C_5$ alkyl and $R_3$ and $R_4$ are both H or a form of 16,17-double bond; alternatively, $R_1$ is either H or $R_1$ and $R_3$ form a 17,20-double bond and $R_2$ is $20-CHO$, $20-C\equiv N$, $20-CH=CH=CH_2$, $20-C\equiv CH$, $20-NH_2$, $20-NH_2$, $20-CH=NOY$, wherein Y is as defined above, and $R_4$ is H if $R_3$ is in a 17,20-double bond; and $R_5$ is H, a ($C_1$–$C_{10}$) carbonyl or a ($C_1$–$C_{10}$) alkyl; alternatively $R_3$ and $R_4$ may both be H or they may form a 16,17-double bond, in an effective amount and in a pharmaceutically acceptable carrier.

The present invention also provides for additional compositions for inhibiting androgen synthesis in vertebrates comprising compounds of the following formula:

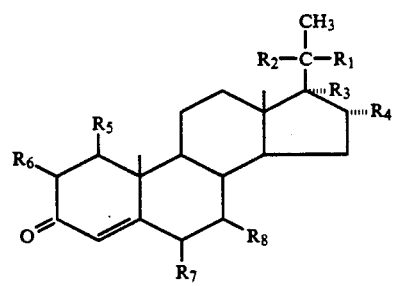

in which $R_1$ and $R_2$ are a (20R)-20,21-epoxy, or (20S)-20,21-epoxy, $=NOY$, wherein Y is H or a $C_1$–$C_5$ alkyl or 20-cyano-20-hydroxy and $R_3$ and $R_4$ are both H or they form a 16,17-double bond; alternatively $R_1$ is either H, or $R_1$ and $R_3$ form a 17,20-double bond and $R_2$ is $20-CHO$, $20-C\equiv N$, $20-CH=CH_2$, $20-C\equiv CH$, $20-NH_2$, or $20-CH=NOY$, wherein Y is as defined above, and $R_4$ is H if $R_3$ is in a 17,20-double bond; alternatively $R_3$ and $R_4$ may both be H or they may form a 16,17-double bond; further in any of the above embodiments, $R_5$ and $R_6$ are both H or they may form a 1,2-double bond and $R_7$ and $R_8$ are both H or they may form a 6,7-double bond, in an effective amount and contained in a pharmaceutically acceptable carrier.

The novel compounds of Formula 1 were synthesized by derivations of pregnenolone precursors through the application of standard techniques given the teachings contained herein. The pregnene-derivative-epoxides were prepared by the addition of sulfur-ylides to the $C_{20}$ carbonyl of the pregnenolone. The pregnene-derivative-hydrazone of Formula 1 was prepared by a condensation of a hydrazine and a pregnenolone occurring at the 20-carbon.

The novel compounds of Formula 2 were synthesized by derivation of either progesterone or its known derivatives through the application of standard techniques given the teachings contained herein. The 20-cyano-17(20)-ene derivative of Formula 2 was synthesized in a two-step reaction. First, a cyanohydrin was added to the 20-ketone of progesterone. The intermediate was then dehydrated to form the 17(20)-ene product. The hydrazone and aldoxime pregnene derivatives of Formula 2 were synthesized by condensation at the aldehyde of 4-pregnen-3-one-20(beta)-carboxaldehyde. The hydrazone derivative was formed by condensation of a hydrazine, while the aldoxime was formed by condensation of an hydroxylamine.

The above-compounds and compositions have valuable pharmacological properties. In particular, the compounds have androgen biosynthesis enzyme inhibitory activities with limited or no side effects. Thus, the compounds and compositions containing the compounds in a pharmaceutically acceptable carrier are useful as a treatment for reducing production of androgens where they have an adverse role in diseases or conditions in vertebrates. Preferably, they are used in mammals and most preferably in humans.

The accompanying drawings, which are incorporated in and constitute a part of this specification, illustrate one embodiment of the invention and, together with the description, serve to explain the principles of the invention.

BRIEF DESCRIPTION OF THE FIGURES

FIG. 1 (a) and FIG. 1(c) contain graphic representations of the inhibition of 17(alpha)-hydroxylase by the compound designated I-23 (FIG. 1(a)) and Ketoconazole, (FIG. 1(c)).

DETAILED DESCRIPTION OF THE INVENTION

Figure 1A:
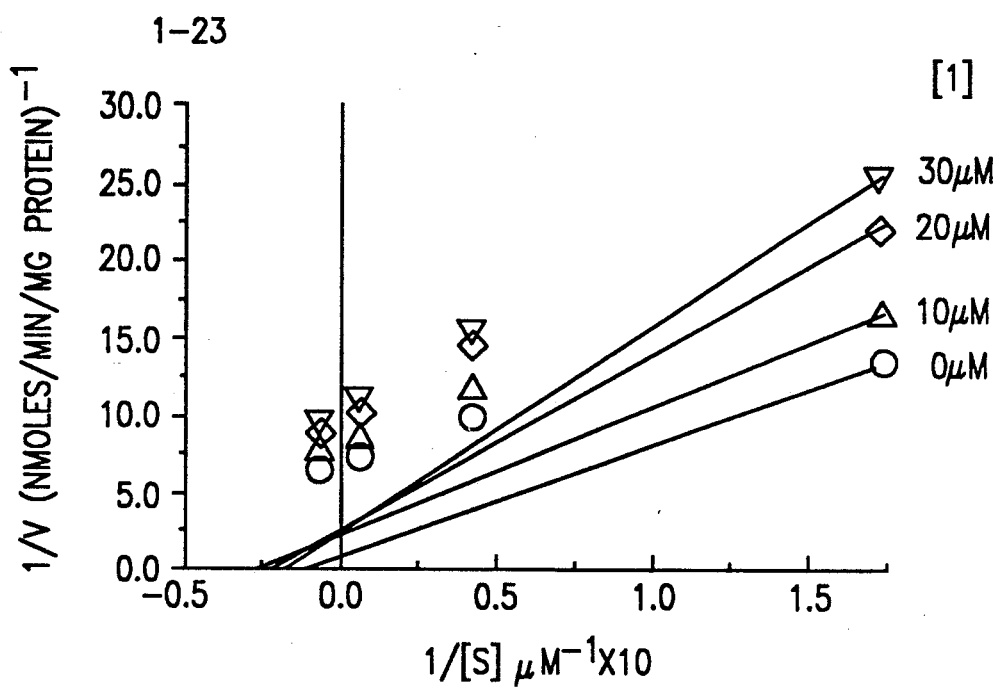
FIG. 1(a) and FIG. 1(c) show Lineweaver-Burk plots of enzyme activities at varying substrate and inhibitors concentrations.

Reference will now be made in detail to the presently preferred embodiments of the invention, which, together with the following examples, serve to explain the principles of the invention. The invention relates to novel 20-substituted-pregnene derivatives that effectively inhibit both the 17(alpha)-hydroxylase/$C_{17,20}$-lyase complex and 5(alpha)-reductase enzyme. By inhibiting both of these enzymes, all androgen synthesis is blocked Inhibition of 17(alpha)-hydroxylase/$C_{17,20}$-lyase blocks production of testosterone, while inhibition of the 5(alpha)-reductase blocks production of dihydrotestosterone. The novel 20-substituted pregnene derivatives are compounds of the following two formulas:

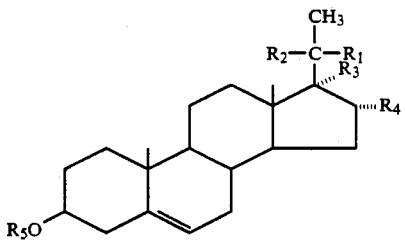

wherein $R_1$ and $R_2$ are a (20R)-20,21-epoxy, a (20S)-20,21 epoxy or =N—N(CH$_3$)$_2$, wherein $R_3$ and $R_4$ are both H or a 16,17-double bond, =N—N (CH$_3$)$_2$, and wherein $R_5$ is H, a ($C_1$-$C_{10}$) carbonyl or a ($C_1$-$C_{10}$) alkyl; and

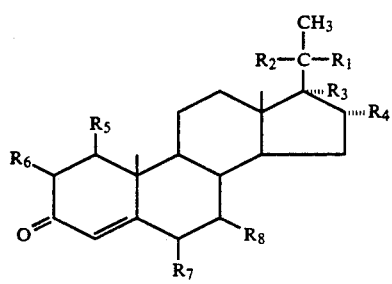

wherein $R_1$ is H or $R_1$ and $R_3$ form a 17,20-double bond, $R_2$ is —CH=N—N(CH$_3$)$_2$, 20—C≡N, or 20—CH=NOY, wherein Y is H or a $C_1$-$C_5$ alkyl, $R_4$ is H if there is a 17,20-double bond; alternatively $R_3$ and $R_4$, can form a 16,17-double bond; further in any of the above embodiments $R_5$ and $R_6$ are both H or they form a 1,2-double bond, and $R_7$ and $R_8$ are both H or they form a 6,7-double bond.

Formula 1 represents the novel compounds having the pregn5-en-3-ol structure. Formula 2 represents the novel compounds having the pregn-4-en-3-one structure. The novel compounds having the structure of Formula 1 are (20R)-20,21-epoxy-20-methyl-5-pregnen-3-(beta)-ol (I-7), (20S)-20,21-epoxy-20-methyl-5-pregnen-(beta)-ol (I-8), and pregn-5,16-dien-3(beta)-ol-20-one N,N-dimethyl hydrazone (I-14).

The novel compounds having the structure of Formula 2 are pregn-4-en-3-oxo-20(beta)-carboxaldehyde N,N-dimethylhyrazone (I-5), pregn-4-en-3-oxo-20(beta)-carboxaldehyde oxime (I-23), and 0-cyano-pregn-4,17(20)-dien-3-one (I-26).

Persons skilled in the art can readily synthesize pharmaceutically acceptable salts of those compounds of formulas 1 and 2 that readily form salts, once given the teachings contained herein. Accordingly, such salts are within the scope of the invention.

The compounds of the invention are useful as a treatment for reducing or inhibiting production of androgens where they have an adverse role in diseases or conditions in vertebrates. The compounds may be administered directly. Preferably, such compounds are in admixture with a pharmaceutically acceptable carrier such as hydroxypropylcellulose, thus providing a composition for reducing or inhibiting androgen production or treating hormone related diseases in vertebrates.

The present invention is further directed to compositions for reducing or inhibiting androgen synthesis. In one embodiment, the compositions of the invention comprise 20-substituted pregnene derivatives of the following formula:

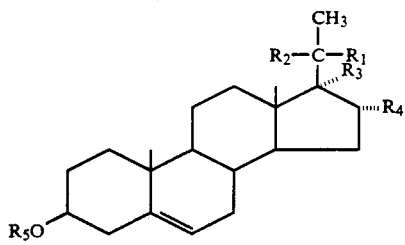

in which $R_1$ and $R_2$ are (20R)-20 21-epoxy (20S)-20 21-epoxy =NOY, wherein Y is H or a $C_1$-$C_5$ alkyl; $R_3$ and $R_4$ are both H or a form of 16,17-double bond; alternatively, $Rl_1$ is either H, or $R_1$ and $R_3$ form a 17,20-double bond and $R_2$ is 20—CHO, 20—C≡N, 20—CH=CH$_2$, 20—C≡CH, 20—NH$_2$, 20—NH$_2$, or 20—CH=NOY, wherein Y is as defined above and $R_4$ is H if $R_3$ is in a 17,20-double bond, and wherein $R_5$ is H, a ($C_1$-$C_{10}$) carbonyl or a ($C_1$-$C_{10}$) alkyl; alternatively $R_3$ and $R_4$ may both be H or may form a 16,17-double bond, in an effective amount and in a pharmaceutically acceptable carrier.

In another embodiment, the compositions comprise 20-substituted pregnene derivatives of compounds of the following formula:

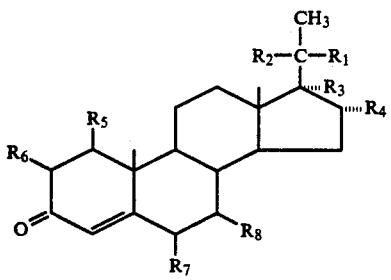

in which $R_1$ and $R_2$ are a (20R)-20,21-epoxy, or (20S)-20,21-epoxy, =NOY, wherein Y is H or a $C_1$-$C_5$ alkyl or 20-cyano-20-hydroxy, and $R_3$ and $R_4$ are both H or they form a 16,17-double bond; alternatively $R_1$ is either H, or $R_1$ and $R_3$ form a 17,20-double bond and $R_2$ is 20—CHO, 20—C≡N, 20—CH=CH$_2$, 20—C≡CH, 20—NH$_2$, or 20CH=NOY, wherein Y is as defined above, and $R_4$ is H if $R_3$ is in a 17,20-double bond; alternatively $R_3$ and $R_4$ may both be H or they may form a 16,17-double bond; further in any of the above embodiments, $R_5$ and $R_6$ are both H or they may form a 1,2-double bond and $R_7$ and $R_8$ are both H or they may form a 6,7-double bond, in an effective amount and contained in a pharmaceutically acceptable carrier.

In making the compositions of the present invention, the active ingredient would usually be mixed with the carrier, or diluted by a carrier, or enclosed within a carrier which may be in the form of a capsule, sachet paper, or other paper or container. The carrier may be a solid, semi-solid, or liquid material which acts as a vehicle, excipient, diluent, or medium for the active ingredient. Thus, the composition may be in the form of tablets, pills, patters, lozenges, sachets, cachets, elixirs, suspensions, emotions, solutions, syrups, aerosols (as a solid or in a liquid medium), ointments containing for example up to 10 percent by weight of the active compounds, soft or hard gelatin capsules, suppositories, sterile injectable solutions, sterile packaged powders, and silastic implants.

Some examples of suitable carriers and dilutants include hydroxypropylcellulose (a suspending agent). The formulations can additionally include, lubricating agents, wetting agents, emulsifying and suspending agents, preserving agents, sweetening agents, flavoring agents, or other active ingredients. The compositions of the invention may be formulated so as to provide quick, sustained, or delayed release of the active ingredient.

The compositions will be preferably formulated in a dosage ranging from about 50 mg to about 500 mg per person/day.

The novel 20-substituted pregnene derivative compounds of Formula 1, i.e., (20R)-20,21-epoxy-20-methyl-5-pregnen-3(beta)-ol, (20S)-20,21-epoxy-20-methyl-5-pregnen-3(beta)-01 and 5,16-pregnadien-3(beta)-01-20-one N,N-dimethyl hydrazone were synthesized according to the following description:

(20R)-20,21-epoxy-20-methyl-5-pregnen-3(beta)ol (I-7)

The suspension of sodium hydride 168 mg (80%, 5.6 mmol), anhydrous dimethyl sulfoxide (DMSO) 3 ml and tetrahydrofuran (THF) 3 ml was stirred for 5 min., then cooled to 0° C. with ice-salt-bath. Trimethylsulfonium iodide 0.58 g (2.8 mmol) was added and the mixture was stirred for 2 h. Pregnenolone acetate 0.5 g (1.4 mmol, in DMSO 4ml and THF 2ml) was added dropwise into the reaction mixture and the ice-bath was removed. The reaction was continued for 12 h at room temperature. Water 5 ml was then added and the mixture was stirred for another 2 h. The reaction mixture was poured into 50 g ice and the product was extracted with dichloromethane. After the removal of solvent, the residue was recrystallized from acetone, then methanol to give white crystals (I-7) 0.2 g with m.p. 160–62° C.

(20S)-20,21-epoxy-20-methyl-5-pregnen-3(beta)-ol (I-8)

The sodium hydride 700 mg (80%, 23.3 mmol) was suspended in anhydrous THF 28 ml. After removing the mineral oil and solvent under nitrogen, trimethyl sulfoxonium iodide 4.8 g (21.8 mmol) and anhydrous THF 24 ml were added. The mixture was refluxed for 3 h, then cooled to 68° C. Pregnenolone acetate 1 g (2.79 mmol) in THF was added dropwise within 20 min.. The mixture was then stirred at room temperature for 17 h. Water 30 ml was added and the products were extracted with ether. After the removal of solvent, the residue was recrystallized from acetone and a mixture of 20R and 20S-epoxides (0.66 g) was obtained. The mixture was chromatographed on a silica gel column and the products were eluted with hexane/ether (8:2–6:4). The yield of 20S-epoxide product was 0.13 g, m.p. 140°–142° C.

5,16-Pregnadien-3(beta)-ol-20-one N,N-dimethyl hydrazone (I-14)

The mixture containing 16-en-pregnenolone 1 g, 1,1-dimethylhydrazine 2ml, ethanol 4 ml and acetic acid (2 drops) was heated to reflux, then stirred overnight at room temperature. Water 30 ml was added, then the precipitate was collected by filtration and dried under vacuum to give 1 g crude product. Recrystallization from methanol then ethanol give 0.68 g pure product with m.p. 167°–69° C.

The novel 20-substituted pregnene derivative compounds of Formula 2, i.e., 4-pregnen-3-oxo-20(beta)-carboxaldehyde N,N-dimethyl hydrazone, 20-cyano-4,17(20)-pregnadiene-3-one, and 4-pregnene-3-oxo-20(beta)-carboxaldehyde oxime, were synthesized in the following described reactions.

4-pregnen-3-oxo-20(beta)-carboxaldehyde N,N-dimethyl hydrazone (I-15)

The mixture containing 4-pregnen-3-one-20(beta)carboxaldehyde 210 mg (0.63 mmol), 1,1-dimethylhydrazine 60 ul (0.79 mmol) and ethanol 4ml was stirred at room temperature for 3 h. Additional dimethylhydrazine 20 ul was added and the reaction was continued for another 1 h. Water 25ml was then added. The precipitate was collected by filtration and dried under vacuum to give 190 mg crude product. Recrystallization from methanol gave 68 mg pure product with m.p. 115°–6° C.

20-cyano-4,17(20)-pregnadien-3-one (I-26)

The procedure of Ercoli and Ruggieri (Gazz. Chim. Ital. 84, 312, 1954, incorporated herein by reference) was followed to prepare 20-cyano-20-hydroxy-4-pregnene-3-one (I-25) from progesterone. Thus, the suspension of progesterone 1.2 g in acetone cyanohydrin 2.4 ml was added and warmed at 40° C. until all the progesterone was dissolved. Four drops of triethylamine was then added. After 2 h the precipitate was filtered and dried to give crude I-25 1.4 g; m.p. 188°–90° C. After recrystallization from ethanol (contained 1% acetic acid), the product was obtained as fine crystals, m.p. 199°–200° C. The mixture containing cyanohydrin (I-25) 0.4 g, methane sulfonyl chloride 1 ml and pyridine 5 ml was stirred at room temperature for 5 h, then at 80° C. for 1 h. Water 20 ml was added and the precipitate was collected. The crude product was chromatographed on silica gel TLC plate (developed by hexane:-/ethyl acetate, 1:1). The yield of I-26 was 80 mg, m.p. 195°–6° C.

4-pregnen-3-oxo-20(beta)-carboxaldehyde oxime (I-23)

To a suspension of sodium acetate 300 mg (3.66 mmol) and methanol 12 ml, hydroxylamine hydrochloride 130 mg (1.87 mmol) was added and the mixture was heated to reflux for 10 min. The upper-phase was then decanted into a flask containing 4-pregnen-3-one-20(beta)-carboxaldehyde (I-16) 600 mg (1.83 mmol) and cooled to 4° C. The mixture was stirred in an ice-bath for 1.5 hours. TLC indicated the reaction was completed (Hexanes/ether 1:2 UV 254nm). Water (20ml) was added to the mixture and the precipitate was collected by filtration and dried. The yield of the crude aldoxime was 597 mg (95.1%). M.p. 182°–85° C. Recrystallization from methanol twice gave colorless needles with m.p. 199°–200° C.

The other compounds included as ingredients of the novel compositions were readily available and were either purchased, for example, from Steraloids or were synthesized according to known reactions.

The compounds and compositions of the present invention are useful for reducing or eliminating androgens in vertebrate species where androgens have a role in a disease or physiological condition. Such diseases or conditions include prostate cancer in men and infertility caused by excess androgen in women. Excess androgens in women also cause polycystic ovaries, hiurtism and polycystic acne.

The vertebrate species include, but are not limited to, humans and other primates, dogs, cats, cattle, swine, fish, chickens, and horses. Preferably, such species are mammals and most preferably humans. Preferably, the compounds and compositions are administered in the same formulations as to humans.

The compounds of the invention may be administered as an androgen biosynthesis inhibitory agent by various routes, including oral, parenteral, rectal, transdermal, subcutaneous, intravenous, intramuscular, or intranasal routes. The preferred routes are oral and any of the injection routes.

The compounds, i.e., the 20-substituted pregnene derivatives, are usually employed in the form of a pharmaceutical composition. The present invention further includes a pharmaceutical composition comprising from about 1 percent to about 95 percent by weight of the pregnene derivatives associated with a pharmaceutically acceptable carrier.

The chemical reactions described above are generally disclosed in terms of their broadest application to the preparation of the compounds of this invention. Occasionally the reactions may not be applicable as described in each compound included within the disclosed scope. The compounds for which this occurs will be readily recognized by those skilled in the art. In such cases, either the reactions can be successfully preformed by a conventional modification known to those skilled in the art, e.g., by appropriate production of interfering groups, by changing to the alternate conventional agents, by routine modification of reaction conditions, etc., or other reactions disclosed herein or otherwise conventional will be applicable to the preparation of the corresponding compounds in this invention. In all the preparative methods, all starting compounds are known or readily preparedly from known starting materials. It will be understandable that the application of the teachings of the present invention to a specific problem or environment will be within the capabilities of one having the ordinary skill in the art in light of the teachings contained herein. Examples of the products of the present invention and processes for their preparation and use appear in the following examples.

EXAMPLE 1

Synthesis and Evaluation of
4-pregnen-3-oxo-20(beta)-carboxaldehyde oxime (I-23)

Chemicals

[4-$^{14}$C]-progesterone (60mCi/mmol), [1,2,6,7,-$^3$H]progesterone (109.3 Ci/mmol), [1,2,6,7-$^3$H]androstenedione (85.4Ci/mmol), [7-$^3$H]-testosterone (23.3Ci/mmol), [4-$^{14}$C]-testosterone (51.4mCi/mmol) were purchased from New England Nuclear Corp. (Boston, Mass.). 17(alpha)-hydroxy-[1,2,6,7-$^3$H]-progesterone (74Ci/mmol) and [4-$^{14}$C]-androstenedione (59mCi/mmol) were purchased from Amersham Corp. (Arlington Heights, Ill.). The purity of the radioactive chemicals was checked by TLC or HPLC prior to use and impure chemicals were purified by TLC. The 4-Pregnen-3-one-20-carboxaldehyde and other steroid compounds were purchased from Steraloids Inc. (Wilton, N.H.). Ketoconazole was purchased from Sigma Chemical Co. (St. Louis, Mo.). The N,N-diethyl-4-methyl-3-oxo-4-aza-5(alpha)-androstane-17(beta)-carboxyamide (4-MA) was a gift from Dr. G. Rasmusson (Merck, Sharp and Dohme Research Laboratories, Rahway, N.J.). 4-hydroxy androstenedione (H-OAA) was prepared as described previously. All other chemicals were purchased from either Sigma Chemical Co. or Aldrich Chemical Co. (Milwaukee, Wis.) and were analytical grade or HPLC grade (for HPLC chromatography). Si250F-PA silica gel TLC plates were from J.T. Baker Inc. Phillipsburg, N.J. Scintillation cocktail 3a70B was purchased from RPI Corp. Mount Prospect, Ill. Steroids-$^{125}$I diagnostic kits for radioimmunoassay (RIA) were purchased from ICN Biochemicals, Inc. (Costa Mesa, Calif.). A Rackbeta II liquid scintillation counter (LKB) was employed to measure tritium and $^{14}$C and a Automatic gamma counter for $^{125}$I (LKB Wallac Oy. Finland).

Chemical Analysis

Melting points were determined on a Fisher-Johns melting point apparatus and were uncorrected. The structures of compounds were determined by their IR, 1H-NMR (GENMR QE 300) and MS spectra.

Preparation of
4-pregnen-3-oxo-20(beta)-carboxaldehyde oxime (I-23)

To a suspension of sodium acetate 300 mg ( 3.66 mmol) and methanol 12 ml, hydroxylamine hydrochloride 130 mg ( 1.87 mmol) was added and the mixture was heated to reflux for 10 min. The upper-phase was then decanted into a flask containing 4-pregnen-3-one-20(beta)-carboxaldehyde 600 mg (1.83 mmol) and cooled to 4° C. The mixture was stirred in an ice-bath for 1.5 hours. TLC indicated the reaction was completed (Hexanes/ether 1:2 UV 254nm). Water (20ml) was added to the mixture and the precipitate was collected by filtration and dried. The yield of the crude aldoxime was 597 mg (95.1 %). M.p. 182°–85° C. Recrystallization from methanol twice gave colorless needles with m.p. 199°–200° C.

Analyses: Calcd($C_{22}H_{33}NO_2$), C, 76.92; H, 9.68; N, 4.08. found, C, 76.54: H, 9.79; N, 4.09. $^1$H-NMR ($CDCl_3$): delta 7.24 (1H, d, 22-H), 5.73 (1H, s, 4-H), 1.19 (3H, s, 19-$CH_3$), 1.12 (3H, d, 21-$CH_3$), 0.76 (3H, s, 18-$CH_3$). MS m/e: 325 (M-$H_2O$).

Enzyme Preparations and Assays

Rat Testicular microsomes

Testes were obtained from 220°–250g adult male Sprague-Dawley rats (Charles River), immediately frozen in liquid nitrogen and stored at −70° C. After thawing in the ice bath, the testes were minced and homogenized in 0.25M sucrose (1:4 w/v), then centrifuged at 12,000×g for 30 min and the resulting supernatant centrifuged at 105,000×g for one hour. The supernatant was then decanted and the pellet containing the microsomes was resuspended in 0.1M sodium phosphate buffer (pH 7.4) (2.5g wet weight of tissue/ 2 ml buffer). All the above procedures were performed at 4C. The microsomal fraction was stored at −70C. Just before use, microsomes were diluted to the concentration of 1.25 g wet weight of tissue/10 ml phosphate buffer.

Human prostate homogenates

Tissues from patients with benign prostatic hypertrophy (BPH) were obtained fresh from the Pathology Department of University of Maryland and stored at −70° C. until assayed. Tissue was homogenized in 0.1M phosphate buffer (60 mg wet weight of tissue/ ml buffer, pH 7.4) at 4C and the homogenates were diluted with an equal volume of buffer before use.

The protein concentrations of tissue used in each assay were determined by the method of Lowry et al [12].

Enzyme Assays

17(alpha)hydroxylase: The 17(alpha)hydroxylase activity was measured by incubation of the substrate [4$^{14}$C]-progesterone (various concentration, 10$^5$dpm) with 50 microliters of an NADPH generating system (NADP 0.65 mM; glucose-6-phosphate 7.1 mM; glucose-6-phosphate dehydrogenase 1.25 IU in 50 microliters phosphate buffer) and approximately 1 mg rat testicular microsomal protein in 450 microliters phosphate buffer, pH 7.4, for 30 min under oxygen at 37° C. The incubation was stopped by cooling the mixture in an ice bath and adding 2 ml ether to each incubation tube. The $^3$H-labelled steriods (progesterone P4; 17(alpha)-hydroxyprogesterone 17OHP4, androstenedione A and testosterone T, 8,000dpm each) were added as recovery markers and the steroids were extracted with ether (2 ml×3). The ether was evaporated with air. Steroid carriers (P4, 17-OHP4, A and T, 4 micrograms each) were added to the extracts which were then applied to thin layer chromatography (TLC) plates for separation of the steroids. After development for 1.5 hours in hexanes/ethyl acetate, 65:35(v/v), the steroids were located by UV (254 nm) absorption, scraped off and eluted into scintillation vials with ether. After evaporating the ether, the steroids were dissolved in counting cocktail and the radioactivity measured. The recovery of steroids calculated from the $^3$H-labelled markers was between 80 to 90 percent and the enzyme activity was determined from the percentage conversion of [4-$C^{14}$]-progesterone to 17OHP4, A and T.

$C^{17,20}$-Lyase: The procedure for measurement of the $C_{17,20}$-lyase was similar to the procedure for the 17(alpha)-hydroxylase, except that the substrate was 17(alpha)-hydroxy-[[1,2,6,7-$^3$H]-progesterone (various concentration, 10$^5$dpm) and recovery markers were [4-$^{14}$C]-labelled steroids. Carrier steroids (17OHP4, A and T) were also added to locate the product areas on the TLC plates. The enzyme activity was determined from the percent conversion of 17(alpha)-hydroxy-[1,2,6,7-3H]-progesterone to A and T.

The purity of each steroid on the TLC was confirmed by two methods. First, the percent conversion of each compound in a half amount of the extract from one incubation were compared after separation of TLC and HPLC. The HPLC procedure has been described in detail previously [13]. The solvent system used was methanol/acetonitrile/water (15.6:36.4:48). The flow rate was 1 ml/min and pressure 2200 psi, the retention time of these steroids was P4 38.3 min, 17OHP4 15.93 min, A 14.33 min, and T 11.43 min, respectively. Secondly, after the first separation by TLC in solvent system A (hexane/ethyl acetate 65:35), the eluted steroids were chromatographed in solvent system B (chloroform/acetonitrile, 85:15).

5(alpha)-reductase: [7-$^3$H]testosterone (10$^6$ dpm) was incubated for 30 minutes at 37° C. with the NADPH generating system, homogenate of human prostatic tissue (30mg wet weight of tissue/1 ml buffer) and the candidate inhibitors at concentrations ranging from 0.1–10uM. Steroids $^{14}$C]-labelled (T, A and dihydrotestosterone, DHT) and authentic markers (T, A, DHT, 5(alpha)-androstane-3(alpha)-diol and -3(beta)-diol, the diols) were added to the incubations. The steroids were extracted with ether and the extracts chromatographed on TLC (chloroform: ether 95:5). The DHT and the diols were located from their markers after exposure of the plate to iodine vapor. The steroids were scraped from the plate and radioactivity measured. In order to confirm the purity of DHT, portions of several samples were rechromatographed on TLC (ether: hexanes 1:2). Results were calculated from the percentage conversion of [7-$^3$H]testosterone to DHT and the diols.

Determination of Km and Ki

The kinetic parameters for the 17(alpha)-hydroxylase, the $C_{17,20}$-lyase and the 5(alpha)-reductase were obtained by Lineweaver-Burk plots at various substrate and inhibitor concentration.

In Vivo Studies

A group of 8 adult male Sprague-Dawley rats were injected sc with vehicle (0.3% hydroxypropyl cellulose, HPC) and a group of 8 rats were injected sc with a suspension of the compound I-23 in HPC (50 mg/kg body weight/day) every 24 hours for 21 days. The rats were autopsied at the last day, the ventral prostates and blood samples were collected. The prostate tissues were stored at −70° C. and the sera were separated first by centrifugation at 2,200 rpm, then stored at −15° C. until assayed. The DHT levels in the rat prostates were measured by radioimmunoassay (RIA) using testosterone/-dihydrotestosterone RIA kit from Amersham Co. (Illinois). The testosterone levels in the rat sera were measured by using the [$^{125}$I]-testosterone diagnostic kits (ICN Biochemics Inc.). The results obtained were analyzed by using Student t test.

Results

In rat testicular microsomes, the Km values determined for the 17(alpha)-hydroxylase was 33.85 uM and for the lyase was 4.55 uM; $V_{max}$ values were 420 and 180 pmole/min/mg protein, respectively.

Figure 1B:
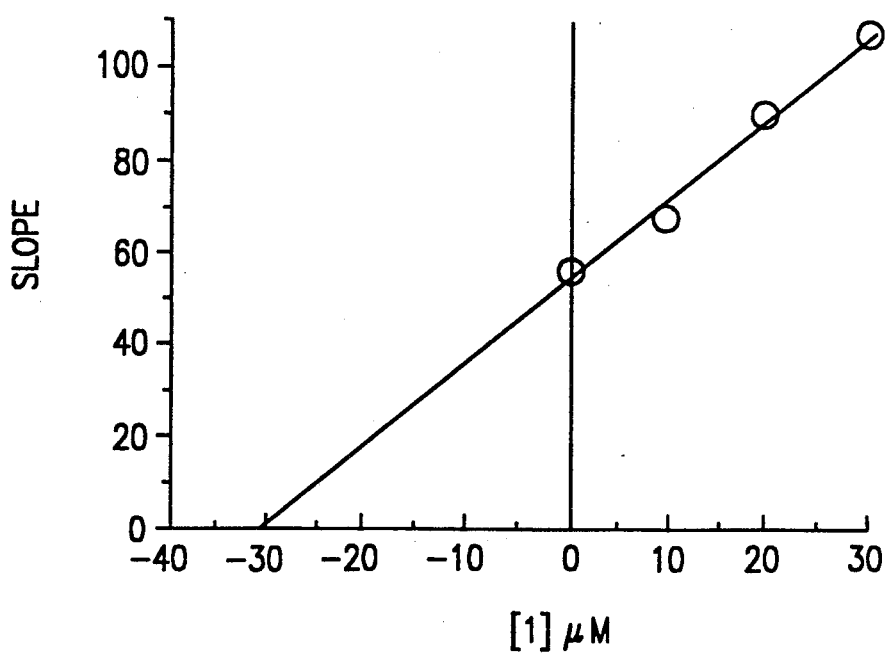
FIGS. 1(b) and FIG. 1(d) show a replot of the slope of each reciprocal plot versus [I].
Figure 1C:
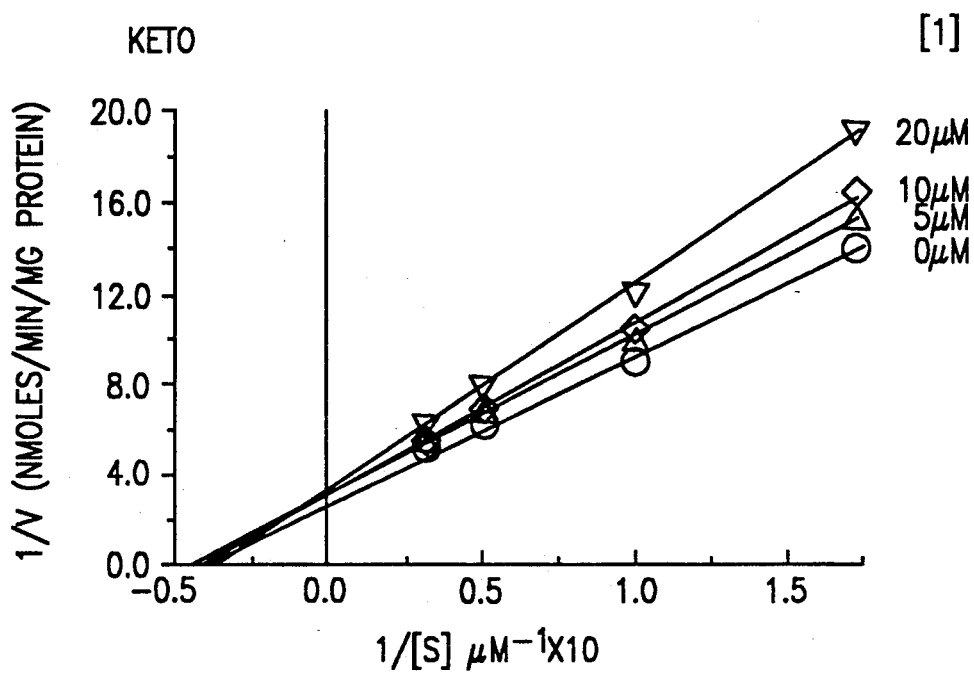
Figure 1D:
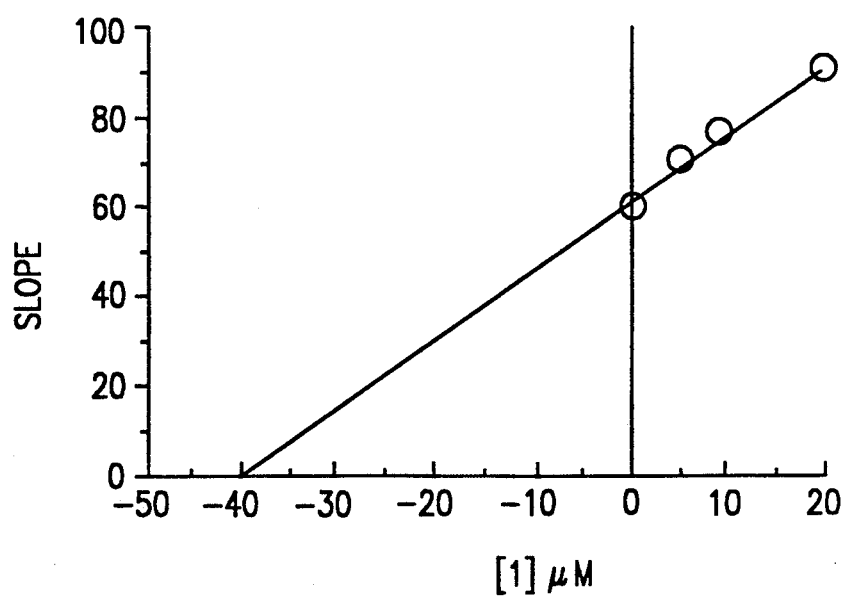
Figure 2A:
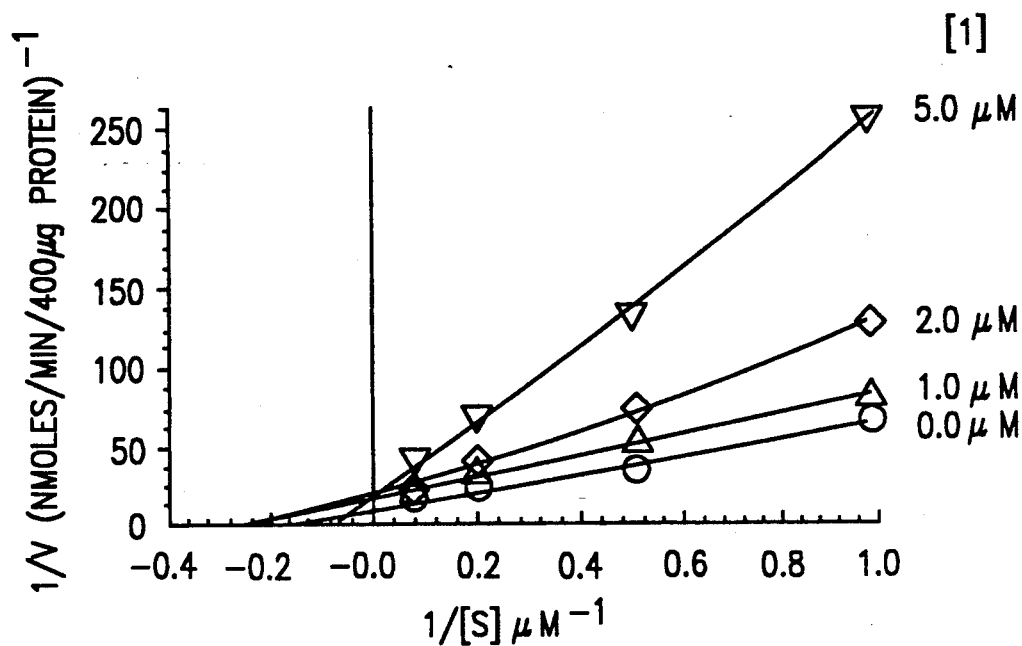
FIGS. 2(a), (b), (c) and (d) refer to same plot methods as FIGS. 1 (a) (b), (c) and (d), respectively, indicating I-23 is more potent than Ketoconazole.
Figure 2B:
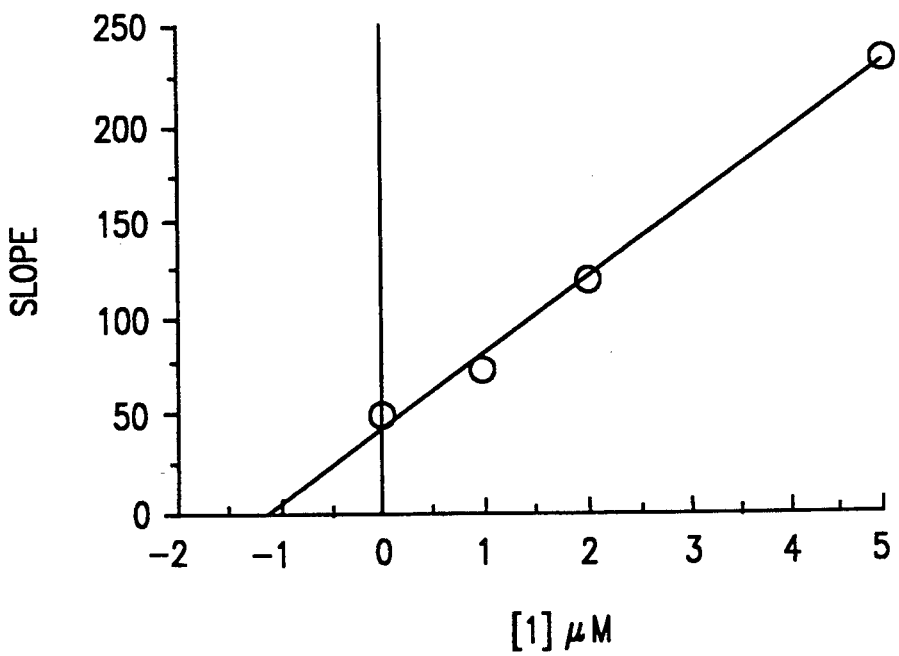
FIG. 2 (a) and FIG. 2(c) contains graphic representations of the Inhibition of $C_{17,20}$-lyase by the compound designated I-23, (FIG. 2(a)) and Ketoconazole, (FIG. 2(c)).
Figure 2C:
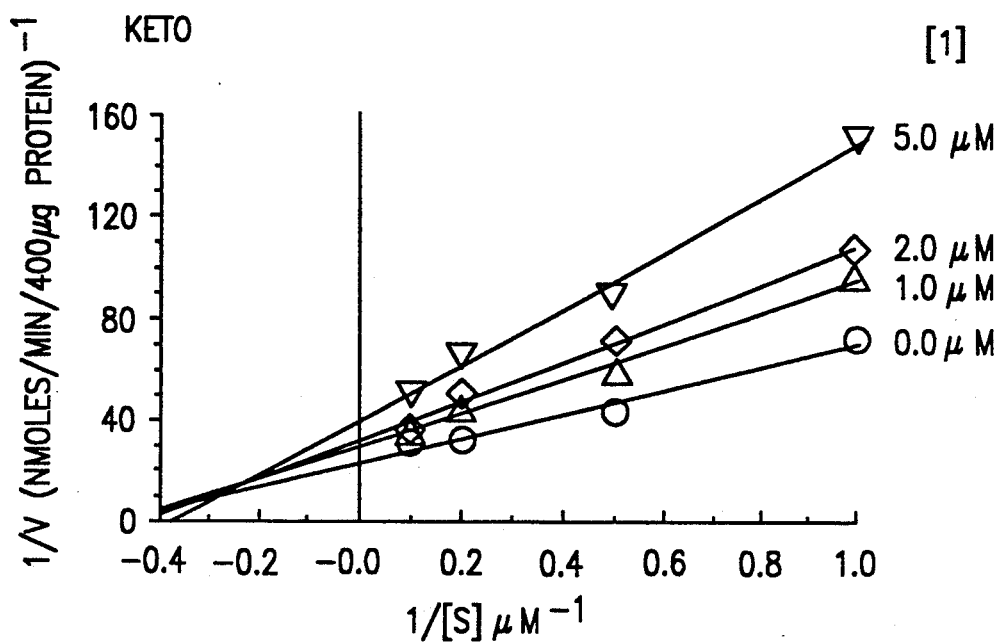
Figure 2D:
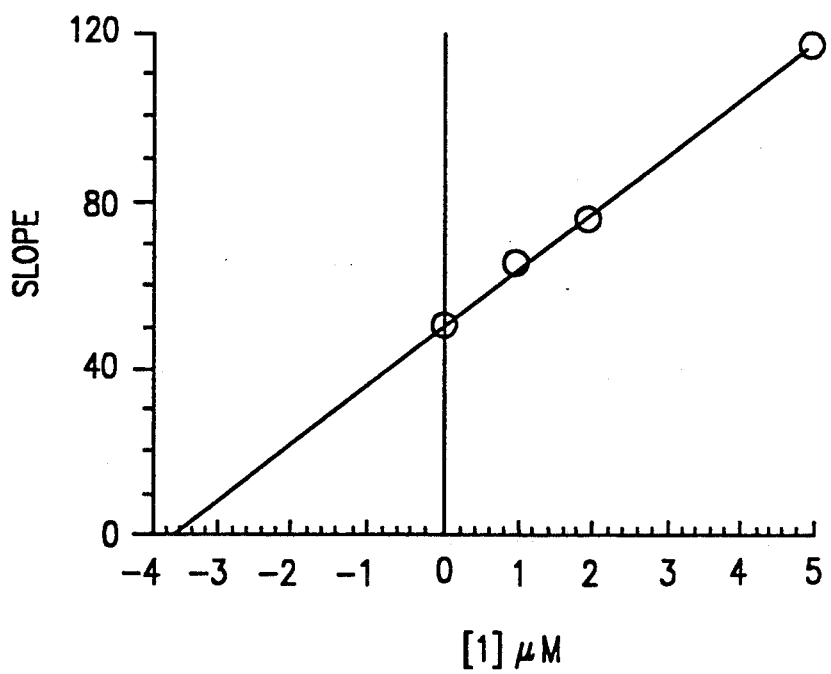

The compound 4-pregnen-3-one-20(beta)-aldoxime (I-23) showed competitive inhibition for both the hydroxlase and the lyase, with a Ki value of 31.2 uM and of 1.07 uM, respectively, (FIG. 1, FIG. 2 and Table 1). The Ki value for the lyase was significantly below the related Km value. Thus, 4-pregnen-3-one-20(beta)-aldoxime is a more specific inhibitor for the lyase than for the hydroxylase. In comparison, the Ki values of 17(alpha)-hydroxylase and $C_{17,20}$-lyase for ketoconazole were 39.5uM and 3.6uM, respectively, which are similar to the Km values of the enzymes. Also tested was 4-MA, known to be a 5(alpha)-reductase inhibitor [14] and 4-OHA, an aromatase inhibitor [15], but these compounds did not show any inhibition of the 17(alpha)-hydroxylase/17,20-lyase enzyme.

The above compounds were also evaluated as inhibitors of 5(alpha)-reductase in human prostatic tissue. Due to the availability of tissue from patients with BPH, rather than from those with prostatic cancer or normal subjects, the benign tissue as a source of prostatic 5(alpha)-reductase was used. The Km value for the enzyme was 40 nM and the V max value was 1.5 pmole/min/mg protein. As shown in Table 1, compound 4-pregnen-3-one-20(beta)-aldoxime (I-23) caused a reduction in the conversion of testosterone into DHT; the Ki value was determined to be 9.1 nM. In comparison the Ki value of 4-MA for the 5(alpha)-reductase was 5.4 nM. Ketoconazole did not inhibit 5(alpha)-reductase in the human prostate.

The 4-pregnen-3-one-20(beta)-aldoxime was also studied for its effect on male rats in vivo. Male rats were daily treated with the compound at the dose of 50 mg/kg body weight injected subcutaneously for 21 days. The daily treatment significantly ($P<0.02$) reduced the concentration of DHT in the prostate. The DHT value for the control rats (n=8) was 1369.1±193.5 pg/100 mg tissue and for the treated rats (n=8) was 760.1=96.2 pg/100 mg tissue. The serum testosterone of these rats was measured as well. The mean control value (n=8) was 4.03±0.64 ng/ml serum, whereas the value for the treated rats (n=8) was 1.60±0.37 ng/ml serum, which was significantly reduced ($P<0.005$). These results indicate that the aldoxime compound is inhibiting both the 17(alpha)-hydroxylase/lyase, as demonstrated by the testosterone levels and the 5(alpha)-reductase, as demonstrated by the DHT values in vivo.

Discussion

The 17(alpha)-hydroxylation and removal of the $C_{17,20}$ side-chain have been reported as two reactions catalyzed by a single protein [16,17]. It was observed that the Km values for these two enzymatic reactions were significantly different. The Km value for the hydroxylase was much greater than for the lyase, which is consistent with high concentration of endogenous progesterone. The results shown in Table 1 indicate that 4-pregnen-3-one-20(beta)-aldoxime preferentially inhibited the lyase rather than the hydroxylase step. According to the Ki values, 4-pregnen-3-one-20(beta)-aldoxime is approximately 3.5-fold more potent than ketoconazole for rat testicular $C_{17,20}$-lyase.

The in vivo results demonstrate that 4-pregnene-3-one-20(beta)-aldoxime is effective in reducing plasma testosterone concentrations and prostatic DHT levels in rats.

The 5(alpha)-reductase inhibitors, 4-MA and finasteride, were noted to increase testosterone levels [18]. Although this effect may be beneficial in treating men with BPH without causing gynecomastia and impotence, inhibition of all androgen production is an important goal of treatment for prostatic cancer. The 20-substituted-pregnene derivatives, of which 4-pregnen-3-one20(beta)-aldoxime is an example, may be of value in this treatment because of their dual action in reducing androgen production by inhibiting synthesis of the substrate (testosterone) and the activity of the 5(alpha)-reductase.

TABLE 1

Inhibition of Rat Testicular 17(alpha)-Hydroxylase[1], $C_{17,20}$-Lyase[2] and Human Prostatic 5(alpha)-Reductase[3]

| Compound | 17(alpha)-hydroxylase Ki(μM) | $C_{17,20}$-lyase Ki(μM) | 5(alpha)-reductase Ki(μM) |
|---|---|---|---|
| I-23 | 31.20 | 1.07 | 9.10 |
| Ketoconazole | 39.50 | 3.60 | N.I.[4] |
| 4-MA | N.I | N.I. | 5.41 |

[1] Incubation of [4-$^{14}$C]-progesterone (various concentration, $10^5$dpm), various concentration of inhibitors, with rat testis microsome (approximately 1 mg protein) and NADPH generating system was carried out at 37 C. under $O_2$ for 30 min. The apparent Km for this enzyme was 33.85 μM, the Vmax was 420 pmole/min/mg protein.
[2] 17(alpha)-hydroxy[1,2,6,7-$^3$H]-progesterone (various concentration, $10^5$ dpm) was used as the substrate. Other conditions were same as above. The apparent Km for this enzyme was 4.55 μM, the Vmax was 180 pmole/min/mg protein.
[3] Incubation of [7-$^3$H]-testosterone (various concentrations, 7 × $10^5$ dpm), various concentration of inhibitors, with human prostatic (BPH) tissue homogenates (30 mg fresh tissue/1.0 ml phosphate buffer). Other conditions were same as above. The apparent Km for this enzyme was 40 nM, the Vmax was 1.5 pmole/min/mg protein,
[4] N.I. refer to no inhibition.

EXAMPLES 2 and 3

Evaluation of 4-pregnen-3-one-20(beta)carboxaldehyde (I-16) and 20-cyano-20-hydroxy-4-pregnen-3-one (I-25)

Compounds I-16 and I-25 were synthesized according to known procedures. The compounds were then assayed for their ability to inhibit the 17(alpha)-hydroxylase/$C_{17,20}$-lyase enzyme and the 5(alpha)-reductase enzyme. The hydroxylase/lyase assay was carried out by incubation of [21-$^{14}$C]-progesterone (40 microM, 70,000 dpm) and candidate inhibitors with rat testis homogenates (2.7 mg protein in 0.5 ml phosphate buffer), NADPH generating system under oxygen for 45 minutes. The enzyme activity was measured according to the conversion of progesterone to the product of $C_{17,20}$-side chain cleavage ([2-$^{14}$C]-acetic acid). The human 5(alpha)-reductase assay was carried out by incubation of [7-$^3$H]-testosterone (0.32 microCi, 23.3 Ci/mmol) various concentration of inhibitors with BPH homogenates (30 mg fresh tissue/1.0 ml phosphate buffer) at 37° C. under $O^2$ for 2 hours. The results were based on the TLC separation.

The results of the two assays are combined in Table 2.

TABLE 2

| Compound | % Inhibition of 17(alpha)hydroxylase/lyase | | Inhibition of 5(alpha)-reductase |
|---|---|---|---|
| | [I] = [S] | [I] = 10 × [S] | IC$_{50}$ (microM) |
| I-16 | 61.76 | 89.95 | 1.4 |
| I-25 | 50.63 | 89.32 | 0.9 |
| Keto | 31.53 | 65.80 | no inhibition |
| 4-MA | No inhibition | No inhibition | 0.3 |

EXAMPLE 4

Evaluation of Other 20-substituted-pregnene derivatives

Other 20-substituted-pregnene derivatives were tested for their inhibition of 17(alpha)-hydroxylase/C$_{17,20}$-lyase. The assay was performed by incubation of rat testicular homogenates (prepared from 220-250g adult male Sprague-Dawley rats, approx. 3.5 mg protein) with [21-$^{14}$C]progesterone (40uM, 5×10$^4$ dpm), NADPH generating system and candidate inhibitors in phosphate buffer (pH 7.4, total volume 500ul) under oxygen for 45 min at 37° C. Two ml of choroform was added to each tube to stop the reaction. The steriods were extracted with chloroform and the aqueous phase was treated with charcoal. The side chain cleavage product [2-$^{14}$C]acetic acid in the aqueous phase was mixed with 3a70B counting cocktail and counted on the Rack Beta II liquid scintillation counter. The enzyme activity was determined from the conversion of progesterone P4 to [2-$^{14}$C]acetic acid.

The results of the assay are shown in Table 3.

TABLE 3

Inhibition of rat testicular 17(alpha)-hydroxylase/C$_{17,20}$-lyase by steriod compounds[1]

| Based Structure | Compound | Substitutents | Inhibition of 17(alpha)-hydroxylase/C$_{17,20}$-lyase (%) | |
|---|---|---|---|---|
| | | | [I] = [S] | [I] = 10 × [S] |
| Pregn-5-en-3(beta)-ol (Compounds of formula 1) | I-1 | 20-one oxime | 14.98 | 29.19 |
| | I-5* | 16-en-20-one oxime | 25.22 | 51.82 |
| | I-7 | (20R)-20,21-epoxy-20-methyl | 21.64 | 28.30 |
| | I-8 | (20S)-20,21-epoxy-20-methyl | 16.30 | 29.35 |
| | I-9 | 20(alpha)-amino | 13.60 | 27.26 |
| | I-10 | 20(beta)-amino | 8.54 | 33.81 |
| | I-12 | 20-one-hydrazine | 8.55 | 25.87 |
| | I-14 | 16-en-20-one N,N-dimethyl hydrazone | 10.21 | 2.34 |
| | I-28 | 20-ene | 13.51 | 18.27 |
| | I-29 | 20-yne | 8.26 | 3.84 |
| Pregn-4-en-3-one (Compounds of formula 2) | I-15 | 20(beta)-carboxaldehyde N,N-dimethylhydrazone | 22.36 | 52.66 |
| | I-18* | 16(alpha),17(alpha)-epoxy-20-one | 26.46 | 64.19 |
| | I-23 | 20(beta)-carboxaldehyde oxime | 39.26 | 83.96 |
| | I-24 | 20(beta)-Cyano-3-enol acetate | 33.59 | 67.17 |
| | I-26 | 17(20)-en-20-cyano | 53.54 | 89.74 |

[1]The compounds marked with "*" were purchased from Steraloids Inc. (Wilton, N.H.). Ketoconazole was from Sigma Chemical Co. (St. Louis, Mo). All other compounds were synthesized in the laboratory by either known or above-described routes.

While the invention has been described with reference to specific embodiments, it will be apparent to those skilled in the art that many alternatives, modifications and variations may be made. Accordingly, it is intended to embrace all such alternatives, modifications and variations that may fall within the spirit and scope of the appended claims.

REFERENCES

1. Barrie, S. E., Rowlands M. G., Foster A. B. and Jarman M.: J. Steroid Biochem. 33 (1989) 1191-1195.
2. McCague R., Rowlands M. G., Barrie S. E. and Houghton J.: J. Med. Chem. 33 (1990) 3050-3055.
3. Jarman M., Barrie S. E., Deadman J. J., Houghton J. and McCague R.: J. Med. Chem 33 (1990) 2452-2455.
4. Ayub M., and Levell M. J.: J. Steroid Biochem. 28 (1987) 521-531.
5. Nakajin S., Takahashi K. and Shinoda M.: Chem Pharm. Bull. 37(1989) 1855-1858.
6. Nakajin S., Takahashi K. and Shinoda M.: Yakugaku Zasshi. 108 (1988) 1188-1195 (Japan).
7. Angelastro M. R., Laughlin M. E., Schatzman G. L., Bey P. and Blohm T. R.: Biochem. Biophys. Res. Commun. 162(1989)1571-1577.
8. De Coster R., Coene M. C., Van Camp C., Van Camp K., Beerens D., and Cools W., J. Enzyme Inhibition, 2(1989) 261-268.
9. Rajfer, J. R., Sikka, S. C.; Rivera, F.; Handelsman, D. J. J.Clin. Endocrinol. Metab.63(1986) 1193-1198.
10. Trachtenberg J.: J. Urol.132(1984) 61-63.
11. Williams G., Kerle D. J., Doble A. Dunlop H., Smith C., Allen J., Yeo T. and Bloom S. R. Br. J. Urol. 58(1986)45-51.1.
12. Lowry O.H., Roseborough N. S., Farr A.. and Randall R. S.: J. Biol. Chem 193)1951) 265-275.
13. Brodie A. M. H., Son C., King D. A., Meyer K. M. and Insker S. E. Cancer Research 49(1989)6551-6555.
14. Rasmusson, G. H., Reynolds, G. F., Steinberg, N. G., Walton, E., Fatel, G. F., Liang, T., Cascieri, M. A., Cheung, A. H., Brooks, J. R. and Berman, C.: J. Med. Chem., 29:2298-2315, 1986.
15. Brodie A. M. H., Schwarzel W., Shaikh A. and Brodie H. J. Endocrinology 100(1977) 1684-1695.
16. Nakajin S., Hall P. F. J. Biol. Chem. 256(1981) 3871-3876.

17. Nakajin S., Shively J. E., Yuan P. M. and Hall P. F. Biochem. 20(1981) 4037–4042.
18. Stoner E. J. Steroid Biochem. Molec. Biol. 37(1990) 375–378.

What is claimed is:

1. A method of reducing or inhibiting the activity of both of the enzymes (17(alpha)-hydroxylase/C17,20-lyase and 5(alpha)-reductase in a vertebrate species comprising the step of administering a pharmaceutically effective amount of a compound according to the following formula or its pharmaceutically acceptable salts:

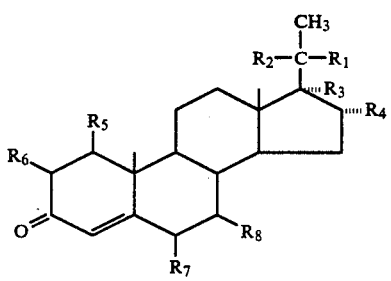

wherein $R_1$ and $R_2$ are (20R)-20,21-epoxy, or (20S)-20,21-epoxy, 20-cyano,-20-hydroxy, or =NOY,
  wherein Y is H or a $C_1$-$C_5$ alkyl; and
  wherein $R_3$ and $R_4$ are both H or a 16,17-double bond; and
  wherein $R_5$ and $R_6$ both H or a 1,2-double bond; and
  wherein $R_7$ and $R_8$ are both H or a 6,7-double bond;
or wherein $R_1$ is H; and
  wherein $R_2$ is 20(beta)—CHO, 20(beta)—CH=CH$_2$, 20(beta)—C≡CH, 20(alpha)—NH$_2$, 20(beta(—NH$_2$, or 20(beta)—CH=NOY, wherein Y is H or a $C_1$-$C_5$ alkyl; and
  wherein $R_3$ and $R_4$ are both H or a 16,17-double bond; and
  wherein $R_5$ and $R_6$ are both H or a 1,2-double bond; and
  wherein $R_7$ and $R_8$ are both H or a 6,7-double bond;
or wherein $R_1$ and $R_3$ are a 17,20-double bond; and
  wherein $R_2$ is 20—CHO, 20—C≡N, 20—CH=CH$_2$, 20—C≡CH, 20—NH$_2$, or 20—CH=NOY, wherein Y is H or a $C_1$-$C_5$ alkyl; and
  wherein $R_4$ is H; and
  wherein $R_5$ and $R_6$ both H or a 1,2-double bond; and
  wherein $R_7$ and $R_8$ are both H or a 6,7-double bond.

2. The method of claim 1, wherein $R_1$ and $R_2$ are 20-cyano-20-hydroxy and wherein $R_3$, $R_4$, $R_5$, $R_6$, $R_7$ and $R_8$ are each H.

3. The method of claim 1, wherein $R_1$ is H; wherein $R_2$ and is 20(beta)—CH=NOY, wherein Y is H; and wherein $R_3$, $R_4$, $R_5$, $R_6$, $R_7$ and $R_8$ are each H.

4. The method of claim 1, wherein said compound is administered orally or by injection.

5. The method of claim 4 wherein said vertebrate species is a human.

* * * * *

UNITED STATES PATENT AND TRADEMARK OFFICE
CERTIFICATE OF CORRECTION

PATENT NO. : 5,264,427
DATED      : November 23, 1993
INVENTOR(S): Brodie et al.

It is certified that error appears in the above-identified patent and that said Letters Patent is hereby corrected as shown below:

Column 1, line 5, delete "CA-27740" and insert therefor --CA-27440--.

Signed and Sealed this

Twenty-seventh Day of September, 1994

Attest:

BRUCE LEHMAN

Attesting Officer

Commissioner of Patents and Trademarks